United States Patent
Admon et al.

(10) Patent No.: US 7,211,405 B2
(45) Date of Patent: May 1, 2007

(54) PLACENTAL PROTEIN 13

(75) Inventors: Arie Admon, Kiryat Tivon (IL); Yoav Paltieli, Haifa (IL); Ronit Slotky, Haifa (IL); Silvia Mandel, Haifa (IL)

(73) Assignee: Diagnostic Technologies Ltd., Haifa (IL)

( * ) Notice: Subject to any disclaimer, the term of this patent is extended or adjusted under 35 U.S.C. 154(b) by 0 days.

(21) Appl. No.: 10/287,639

(22) Filed: Nov. 5, 2002

(65) Prior Publication Data

US 2003/0092188 A1  May 15, 2003

Related U.S. Application Data

(60) Division of application No. 09/601,178, filed on Jan. 31, 2001, and a continuation-in-part of application No. PCT/IL99/00036, filed on Jan. 21, 1999, now Pat. No. 6,548,306.

(30) Foreign Application Priority Data

Jan. 29, 1998 (IL) ..................................... 123098

(51) Int. Cl.
  *G01N 33/567* (2006.01)
  *A61K 38/00* (2006.01)
  *C07K 2/00* (2006.01)
  *C07H 21/04* (2006.01)

(52) U.S. Cl. ..................... 435/7.21; 435/6; 435/7.92; 435/7.93; 530/300; 530/350; 536/23.1; 536/23.4; 536/26.3; 422/50; 422/60; 436/501; 436/518

(58) Field of Classification Search ................ 435/6, 435/7.21, 7.92, 7.93, 440, 970; 436/65, 86.87, 436/501, 503, 504, 510, 512, 514, 518; 530/300, 530/350, 413; 536/23.1, 23.4, 26.3; 422/50, 422/60
See application file for complete search history.

(56) References Cited

U.S. PATENT DOCUMENTS

| | | | |
|---|---|---|---|
| 4,444,879 A * | 4/1984 | Foster et al. .................. | 435/7 |
| 4,500,451 A | 2/1985 | Bohn et al. | |
| 5,198,366 A * | 3/1993 | Silberman .................... | 436/86 |
| 6,548,306 B1 * | 4/2003 | Admon et al. ................ | 436/86 |

FOREIGN PATENT DOCUMENTS

| EP | 0 101 603 | 2/1984 |
|---|---|---|
| EP | 0283606 | 9/1988 |

OTHER PUBLICATIONS

Bohn et al. "Publication and characterization of 2 new soluble placental tissue proteins pp. -13 and pp. -17." Oncodevelopmental Biology and Medicine, 1983, vol. 4, No. 5, pp. 343-350. Abstract Only.*
GenCore version 5.1.6, OM protein search, dated Oct. 8, 2003.*
Suckau et al. "Molecular epitope identification by limited proteolysis of an immoblized antigen-antibody complex and mass spectrometric peptide mapping." PNAS, USA, vol. 87, Dec. 1990, pp. 9848-9852.*
Than et al., "Isolation and Sequence Analysis of cDNA Encoding . . . (pp. 13) . . . ", Placenta, 1999, 20, 703-710.*
Case No. 04-1075 (serial No. 08/822,509) Crish and Eckert.*
EMBL AA7-6870; May 01, 1998.
N.G. Than et al; "Isolation and sequence Analysis of a cDNA Encoding Human Placental..."; Placents (1999); 20, 703-71.

* cited by examiner

*Primary Examiner*—Long V. Le
*Assistant Examiner*—Lisa V. Cook
(74) *Attorney, Agent, or Firm*—Browdy & Neimark, PLLC

(57) ABSTRACT

The full amino acid and DNA sequences of placental protein 13 (PP13) are disclosed. Also described are various PP13 derived peptide fragments, and a recombinant method for the production of PP13. PP13 may be used in a screening and a diagnostic method for pregnancy-related complications.

9 Claims, 3 Drawing Sheets

```
+                    #3
                                  M  S  S  L  P  L  Q  V  D
  1   caattctgaaggtcgccaagaaggagagaacaATGTCTTCTTTACCCCTGCAGGTGGAT F  Y  T  D  M  D  E  D  S  D  I  A  F  R  F  R  V  H  F  G
 60   TTCTACACTGACATGGATGAGGATTCAGATATTGCCTTCCGTTTCCGAGTGCACTTTGGC
                                       #4
      N  H  V  V  M  N  R  R  E  F  G  I  W  M  L  E  E  T  T  D
120   AATCATGTGGTCATGAACAGGCGTGAGTTTGGGATATGGATGTTGGAGGAGACAACAGAC
                             #5                      #6
      Y  V  P  F  E  D  G  K  Q  F  E  L  C  I  Y  V  H  Y  N  E
180   TACGTGCCCTTTGAGGATGGCAAACAATTTGAGCTGTGCATCTACGTACATTACAATGAG Y  E  I  K  V  N  G  H  T  H  L  R  L  C  P  I  E  S  R  H
240   TATGAGATAAAGGTCAATGGGCATACGCATTTACGGCTTTGTCCCATCGAATCCCGNCAT H  L  L  K  M  G  A  S  V  R  G  D  I  F  P  G  P  S  V  C
300   CATTTGTTGAAGATGGGTGCAAGTGTCCGAGGAGATATCTTCCCTGGACCNTCAGTGTGT

V  L  Q  F  ?  G  E  M  I  H
360   GTCTTGCAATTTNAGGGGGAGATGATCCACA
```

FIG. 1

```
5'                                                          *
                                               M  S  S   L  P  V  P
  1 actggactca attctgaagg tcgccaagaa agaaaaaaca ATGTCTTCTT TACCCGTGCC
           #1                             #2                 #3
       Y  K  L   P  V  S   L  S  V   S  C  V   I  I  K   G  T  P  I
 61 ATACAAACTG CCTGTGTCTT TGTCTGTTGG TTCCTGCGTG ATAATCAAAG GGACACCAAT H  S  F   I  N  D   P  Q  L   V  D  F   Y  T  D   M  D  E  D
121 CCACTCTTTT ATCAATGACC CACAGCTGCA GGTGGATTTC TACACTGACA TGGATGAGGA S  D  I   A  F  R   F  R  V   H  F  G  N   H  V  V   M  N  R  R
181 TTCAGATATT GCCTTCCGTT TCCGAGTGCA CTTTGGCAAT CATGTGGTCA TGAACAGGCG
       #4
       E  F  G   I  W  M   L  E  E  T   T  D  Y   V  P  F   E  D  G  K
241 TGAGTTTGGG ATATGGATGT TGGAGGAGAC AACAGACTAC GTGCCCTTTG AGGATGGCAA
       #5                         #6
       Q  F  E   L  C  I   Y  V  H  Y   N  E  Y   E  I  K   V  N  G  I
301 ACAATTTGAG CTGTGCATCT ACGTACATTA CAATGAGTAT GAGATAAAGG TCAATGGCAT
                  #7
       R  I  Y   G  F  V   H  R  I  P   P  S  F   V  K  M   V  Q  V  S
361 ACGCATTTAC GGCTTTGTCC ATCGAATCCC GCCATCATTT GTGAAGATGG TGCAAGTGTC R  D  I   S  L  T   S  V  C   C  N
421 GAGAGATATC TCCCTGACCT CAGTGTGTGT CTGCAATtga gggagatgat cacactcctc
481 attgttgagg aaatccctct ttctacctga ccatgggatt cccagaacct gctaacagaa
541 taatccctgc tcacattttc ccctacactt tgtcattaaa acagcacgaa aactcaaaaa
601 aaaaaaaaaa
```

FIG. 2

```
PP13   1  MSSLPVPYKLPVSLSVGSCVIIKGTPIHSFINDPQLQVDFYTDMDED
          || |||||    ||| || | ||| |   | | | |||||  | | |
EPL    1  MSLLPVPYTEAASLSTGSTVTIKGRPLVCFLNEPYLQVDFHTEMKEE

PP13  48  SDIAFRFRVHFGNHVVMNRREFGIWMLEETTDYVPFEDGKQFELCIY
          ||| |  | | ||  |||| ||  ||||  ||  ||         |||  |
EPL   48  SDIVFHFQVCFGRRVVMNSREYGAWKQQVESKNMPFQDGQEFELSIS

PP13  95  VHYNEYEIKVNGIRIYGFVHRIPPSFVKMVQVSRDISLTSVCVCN
          |    |    |||    |    ||| |   ||| ||| || |||    |
EPL   95  VLPDKYQVMVNGQSSYTFDHRIKPEAVKMVQVWRDISLTKFNVSYLKR
```

FIG. 3

SEQUENCE LISTING

```
<160> NUMBER OF SEQ ID NOS: 17

<210> SEQ ID NO 1
<211> LENGTH: 8
<212> TYPE: PRT
<213> ORGANISM: Homo sapiens

<400> SEQUENCE: 1

Leu Pro Val Ser Leu Ser Val Gly
1               5

<210> SEQ ID NO 2
<211> LENGTH: 4
<212> TYPE: PRT
<213> ORGANISM: Homo sapiens

<400> SEQUENCE: 2

Val Ile Ile Lys
1

<210> SEQ ID NO 3
<211> LENGTH: 17
<212> TYPE: PRT
<213> ORGANISM: Homo sapiens

<400> SEQUENCE: 3

Gly Thr Pro Ile His Ser Phe Ile Asn Asp Pro Gln Leu Gln Val Asp
1               5                   10                  15

Phe

<210> SEQ ID NO 4
<211> LENGTH: 17
<212> TYPE: PRT
<213> ORGANISM: Homo sapiens

<400> SEQUENCE: 4

Glu Phe Gly Ile Trp Met Leu Glu Glu Thr Thr Asp Tyr Val Pro Phe
1               5                   10                  15

Glu

<210> SEQ ID NO 5
<211> LENGTH: 7
<212> TYPE: PRT
<213> ORGANISM: Homo sapiens

<400> SEQUENCE: 5

Gln Phe Glu Leu Cys Ile Tyr
1               5

<210> SEQ ID NO 6
```

```
<211> LENGTH: 6
<212> TYPE: PRT
<213> ORGANISM: Homo sapiens

<400> SEQUENCE: 6

Val His Tyr Asn Glu Tyr
1               5

<210> SEQ ID NO 7
<211> LENGTH: 5
<212> TYPE: PRT
<213> ORGANISM: Homo sapiens

<400> SEQUENCE: 7

Gly Phe Val His Arg
1               5

<210> SEQ ID NO 8
<211> LENGTH: 611
<212> TYPE: DNA
<213> ORGANISM: Homo sapiens

<400> SEQUENCE: 8
actggactca attctgaagg tcgccaagaa agaaaaaaca atgtcttctt tacccgtgcc      60
atacaaactg cctgtgtctt tgtctgttgg ttcctgcgtg ataatcaaag ggacaccaat     120
ccactctttt atcaatgacc cacagctgca ggtggatttc tacactgaca tggatgagga     180
ttcagatatt gccttccgtt tccgagtgca ctttggcaat catgtggtca tgaacaggcg     240
tgagtttggg atatggatgt tggaggagac aacagactac gtgccctttg aggatggcaa     300
acaatttgag ctgtgcatct acgtacatta caatgagtat gagataaagg tcaatggcat     360
acgcatttac ggctttgtcc atcgaatccc gccatcattt gtgaagatgg tgcaagtgtc     420
gagagatatc tccctgacct cagtgtgtgt ctgcaattga gggagatgat cacactcctc     480
attgttgagg aaatccctct ttctacctga ccatgggatt cccagaacct gctaacagaa     540
taatccctgc tcacattttc ccctacactt tgtcattaaa acagcacgaa aactcaaaaa     600
aaaaaaaaaa a                                                          611

<210> SEQ ID NO 9
<211> LENGTH: 139
<212> TYPE: PRT
<213> ORGANISM: Homo sapiens

<400> SEQUENCE: 9

Met Ser Ser Leu Pro Val Pro Tyr Lys Leu Pro Val Ser Leu Ser Val
1               5                   10                  15

Gly Ser Cys Val Ile Ile Lys Gly Thr Pro Ile His Ser Phe Ile Asn
            20                  25                  30

Asp Pro Gln Leu Gln Val Asp Phe Tyr Thr Asp Met Asp Glu Asp Ser
        35                  40                  45

Asp Ile Ala Phe Arg Phe Arg Val His Phe Gly Asn His Val Val Met
    50                  55                  60

Asn Arg Arg Glu Phe Gly Ile Trp Met Leu Glu Glu Thr Thr Asp Tyr
65                  70                  75                  80

Val Pro Phe Glu Asp Gly Lys Gln Phe Glu Leu Cys Ile Tyr Val His
                85                  90                  95

Tyr Asn Glu Tyr Glu Ile Lys Val Asn Gly Ile Arg Ile Tyr Gly Phe
            100                 105                 110
```

Val His Arg Ile Pro Pro Ser Phe Val Lys Met Val Gln Val Ser Arg
    115                 120                 125

Asp Ile Ser Leu Thr Ser Val Cys Val Cys Asn
    130                 135

<210> SEQ ID NO 10
<211> LENGTH: 417
<212> TYPE: DNA
<213> ORGANISM: Homo sapiens

<400> SEQUENCE: 10

```
atgtcttctt tacccgtgcc atacaaactg cctgtgtctt tgtctgttgg ttcctgcgtg      60
ataatcaaag ggacaccaat ccactctttt atcaatgacc cacagctgca ggtggatttc     120
tacactgaca tggatgagga ttcagatatt gccttccgtt ccgagtgca ctttggcaat     180
catgtggtca tgaacaggcg tgagtttggg atatggatgt tggaggagac aacagactac     240
gtgcccttg aggatggcaa acaatttgag ctgtgcatct acgtacatta caatgagtat     300
gagataaagg tcaatggcat acgcatttac ggctttgtcc atcgaatccc gccatcattt     360
gtgaagatgg tgcaagtgtc gagagatatc tccctgacct cagtgtgtgt ctgcaat       417
```

<210> SEQ ID NO 11
<211> LENGTH: 142
<212> TYPE: PRT
<213> ORGANISM: Homo sapiens

<400> SEQUENCE: 11

Met Ser Leu Leu Pro Val Pro Tyr Thr Glu Ala Ala Ser Leu Ser Thr
1               5                   10                  15

Gly Ser Thr Val Thr Ile Lys Gly Arg Pro Leu Val Cys Phe Leu Asn
            20                  25                  30

Glu Pro Tyr Leu Gln Val Asp Phe His Thr Glu Met Lys Glu Glu Ser
        35                  40                  45

Asp Ile Val Phe His Phe Gln Val Cys Phe Gly Arg Arg Val Val Met
    50                  55                  60

Asn Ser Arg Glu Tyr Gly Ala Trp Lys Gln Gln Val Glu Ser Lys Asn
65                  70                  75                  80

Met Pro Phe Gln Asp Gly Gln Glu Phe Glu Leu Ser Ile Ser Val Leu
                85                  90                  95

Pro Asp Lys Tyr Gln Val Met Val Asn Gly Gln Ser Ser Tyr Thr Phe
            100                 105                 110

Asp His Arg Ile Lys Pro Glu Ala Val Lys Met Val Gln Val Trp Arg
        115                 120                 125

Asp Ile Ser Leu Thr Lys Phe Asn Val Ser Tyr Leu Lys Arg
    130                 135                 140

<210> SEQ ID NO 12
<211> LENGTH: 35
<212> TYPE: DNA
<213> ORGANISM: Homo sapiens

<400> SEQUENCE: 12

```
ggccacgcgt cgactagtac ttttttttt ttttt                                35
```

<210> SEQ ID NO 13
<211> LENGTH: 20
<212> TYPE: DNA
<213> ORGANISM: Homo sapiens

```
<400> SEQUENCE: 13
ggccacgcgt cgactagtac                                                   20

<210> SEQ ID NO 14
<211> LENGTH: 23
<212> TYPE: DNA
<213> ORGANISM: Homo sapiens

<400> SEQUENCE: 14
gggatatgga tgttggagga gac                                               23

<210> SEQ ID NO 15
<211> LENGTH: 21
<212> TYPE: DNA
<213> ORGANISM: Homo sapiens

<400> SEQUENCE: 15
gtctcctcca acatccatat c                                                 21

<210> SEQ ID NO 16
<211> LENGTH: 390
<212> TYPE: DNA
<213> ORGANISM: Homo sapiens
<220> FEATURE:
<221> NAME/KEY: misc_feature
<222> LOCATION: (296)..(296)
<223> OTHER INFORMATION: "n" at position 296 is unknown
<220> FEATURE:
<221> NAME/KEY: misc_feature
<222> LOCATION: (350)..(350)
<223> OTHER INFORMATION: "n" at position 350 is unknown
<220> FEATURE:
<221> NAME/KEY: misc_feature
<222> LOCATION: (372)..(372)
<223> OTHER INFORMATION: "n" at position 372 is unknown
<220> FEATURE:
<221> NAME/KEY: CDS
<222> LOCATION: (33)..(389)
<223> OTHER INFORMATION:

<400> SEQUENCE: 16
caattctgaa ggtcgccaag aaggagagaa ca atg tct tct tta ccc ctg cag         53
                                   Met Ser Ser Leu Pro Leu Gln
                                    1               5 gtg gat ttc tac act gac atg gat gag gat tca gat att gcc ttc cgt        101
Val Asp Phe Tyr Thr Asp Met Asp Glu Asp Ser Asp Ile Ala Phe Arg
         10                  15                  20 ttc cga gtg cac ttt ggc aat cat gtg gtc atg aac agg cgt gag ttt        149
Phe Arg Val His Phe Gly Asn His Val Val Met Asn Arg Arg Glu Phe
 25                  30                  35 ggg ata tgg atg ttg gag gag aca aca gac tac gtg ccc ttt gag gat        197
Gly Ile Trp Met Leu Glu Glu Thr Thr Asp Tyr Val Pro Phe Glu Asp
 40                  45                  50                  55 ggc aaa caa ttt gag ctg tgc atc tac gta cat tac aat gag tat gag        245
Gly Lys Gln Phe Glu Leu Cys Ile Tyr Val His Tyr Asn Glu Tyr Glu
                 60                  65                  70 ata aag gtc aat ggg cat acg cat tta cgg ctt tgt ccc atc gaa tcc        293
Ile Lys Val Asn Gly His Thr His Leu Arg Leu Cys Pro Ile Glu Ser
             75                  80                  85 cgn cat cat ttg ttg aag atg ggt gca agt gtc cga gga gat atc ttc        341
Arg His His Leu Leu Lys Met Gly Ala Ser Val Arg Gly Asp Ile Phe
         90                  95                 100 cct gga ccn tca gtg tgt gtc ttg caa ttt nag ggg gag atg atc cac a      390
Pro Gly Pro Ser Val Cys Val Leu Gln Phe Xaa Gly Glu Met Ile His
    105                 110                 115
```

```
<210> SEQ ID NO 17
<211> LENGTH: 119
<212> TYPE: PRT
<213> ORGANISM: Homo sapiens
<220> FEATURE:
<221> NAME/KEY: misc_feature
<222> LOCATION: (114)..(114)
<223> OTHER INFORMATION: The 'Xaa' at location 114 stands for Lys, Glu,
      Gln, or a stop codon.

<400> SEQUENCE: 17

Met Ser Ser Leu Pro Leu Gln Val Asp Phe Tyr Thr Asp Met Asp Glu
1               5                   10                  15

Asp Ser Asp Ile Ala Phe Arg Phe Arg Val His Phe Gly Asn His Val
            20                  25                  30

Val Met Asn Arg Arg Glu Phe Gly Ile Trp Met Leu Glu Glu Thr Thr
        35                  40                  45

Asp Tyr Val Pro Phe Glu Asp Gly Lys Gln Phe Glu Leu Cys Ile Tyr
    50                  55                  60

Val His Tyr Asn Glu Tyr Glu Ile Lys Val Asn Gly His Thr His Leu
65                  70                  75                  80

Arg Leu Cys Pro Ile Glu Ser Arg His His Leu Leu Lys Met Gly Ala
            85                  90                  95

Ser Val Arg Gly Asp Ile Phe Pro Gly Pro Ser Val Cys Val Leu Gln
            100                 105                 110

Phe Xaa Gly Glu Met Ile His
        115
```

PLACENTAL PROTEIN 13

CROSS-REFERENCE TO RELATED APPLICATIONS

The present application is a divisional of application Ser. No. 09/601,178, filed Jan. 31, 2001 now U.S. Pat. No. 6,548,306, which is a national stage under 35 U.S.C. 371 of PCT/IL99/00036, filed Jan. 21, 1999.

FIELD OF THE INVENTION

The present invention relates to a placental protein and its uses.

BACKGROUND OF THE INVENTION

References referred to in the text by a number enclosed by parenthesis are listed at the end of the specification.

The goal of pregnancy management is the delivery of a mature, healthy infant, without encountering complications which can adversely affect the well being of both the mother and the newborn. A significant percentage of pregnancies are affected by various disorders. Among these complications are preterm labor and delivery, intrauterine growth retardation and preeclampsia. These conditions negatively impact the outcome of affected pregnancies, at enormous cost both to the patients as well as to the health system.

Placental Protein 13 (PP13) is a protein which was previously isolated from human placental tissue (U.S. Pat. No. 4,500,451 to Bohn, et al., the contents of which are incorporated herein by reference). The protein was characterized by the following parameters: electrophoretic mobility, isoelectric point, sedimentation coefficient, molecular weight determined by ultracentrifugation, molecular weight determined by SDS-PAGE, extinction coefficient and carbohydrate content. The amino acid composition (residues per 100 residues) was determined but not the amino acid sequence.

PP13 was used to develop an assay for the early stage detection of three specific pregnancy-related disorders: intrauterine growth retardation, preeclampsia and preterm delivery (U.S. Pat. No. 5,198,366 to Silberman). Both a radioimmunoassay (RIA) and an enzyme-linked immunoassay (ELISA) are disclosed using labeled PP13 and anti PP13 antiserum, respectively. No further properties of PP13 are disclosed in the Silberman patent.

BRIEF SUMMARY OF THE INVENTION

It is an object of the present invention to provide a pure PP13 protein.

It is a further object of the present invention to provide a DNA molecule encoding PP13.

It is a still further object of the invention to provide a recombinant method for producing PP13.

Additionally, it is an object of the present invention to provide a diagnostic assay based on PP13 for the early detection of pregnancy complications.

It is another object of the invention to provide immunogenic peptides derived from PP13 which can be used in such a diagnostic assay.

According to one aspect of the present invention, there is provided a protein or polypeptide selected from the group consisting of: (a) Placental Protein 13 (PP13) having the amino acid sequence shown in FIG. 2 (SEQ.ID.NO: 9); (b) a polypeptide having a sequence of amino acids included in PP13 and which binds to antibodies which specifically bind to PP13; (c) a protein or polypeptide of (a) or (b) in which one or more amino acids have been added, deleted or replaced without reducing the ability of the protein or polypeptide to bind antibodies which specifically bind to PP13; and (d) a protein or polypeptide having an amino acid sequence including the amino acid sequence of (a) or (b) or (c).

By another aspect of the present invention, there is provided a DNA molecule encoding the above protein or polypeptide.

According to another aspect of the present invention, there is provided a method of screening for pregnancy-related complications comprising the steps of: (a) providing a serum sample of a pregnant woman; (b) determining the level of PP13 or a peptide derived therefrom in the serum sample. and (c) comparing the determined level with predetermined normal levels for women at the same gestational age, a deviation between the levels being indicative of a pregnancy-related complication.

By one embodiment of the invention, the determination in step (b) is by means of antibodies, preferably monoclonal antibodies, directed against said proteins or polypeptides.

According to yet another aspect of the present invention, there is provided a recombinant method for the production of PP13 comprising inserting said DNA molecule into an expression vector, inserting the expression vector into a host cell, and incubating the host cell under conditions which permit expression of the inserted vector.

The present invention provides for the first time the full amino acid sequence of PP13, as well as its full cDNA sequence. This information can be utilized in a number of applications. For example, modified PP13 protein homologues and analogues can be produced in which one or more amino acids have been added, deleted or replaced, the modified protein typically retaining 75% homology with PP13. Methods for modifying the amino acid sequence of a protein whose full sequence is known are well known in the art, and include e.g. chemical synthesis, controlled mutagenesis and recombinant methods. Such modified proteins may have superior properties over the natural PP13 in various applications, such as superior immunogenicity or immunospecificity (e.g. the modified protein may be devoid of immune epitopes common with other proteins) for use in an immunoassay for the early detection of pregnancy-related disorders as described in Silberman.

Furthermore, peptide fragments may be prepared from PP13 and such peptides may be modified as described above with respect to the full protein. These peptides may also be used in various applications. For example, it is well known that immunogenic proteins have specific amino acid sequences or epitopes which induce the immune system to mount an immune response to the protein. The above peptides may be tested for the presence of an epitope of PP13 so as to identify the epitope(s). A peptide containing an epitope may then be used in an immunoassay for pregnancy disorders. A number of PP13-derived peptides are disclosed below.

The pure PP13 protein or a derived peptide may be used to prepare antibodies to PP13. Either polyclonal or monoclonal antibodies may be produced by standard methods well known to the skilled artisan.

Both the antibodies as well as the proteins and peptides may be used to prepare diagnostic or screening assays for the detection of pregnancy-related complications such as intrauterine growth retardation, preterm delivery and preeclampsia. Examples of such assays are detailed in Silberman, the contents of which are incorporated herein by reference, and include radioimmunoassays (RIA) and enzyme-linked immunoassays (ELISA). In general, such an assay will include the steps of obtaining a serum sample of a pregnant woman, determining the level of PP13 or of a derived peptide in the serum sample by the immunoassay, and comparing the determined level with pre-determined normal levels for women at the same gestational age. A statistically significant deviation between the levels will be indicative of a pregnancy-related complication.

As mentioned above, the full cDNA of PP13 is disclosed here for the first time. Since the full amino acid sequence of PP13 is also disclosed, various DNA molecules encoding PP13 may be prepared due to the degeneracy of the genetic code. In addition, DNA molecules capable of hybridizing to these DNA molecules under stringent conditions may also be prepared. The DNA molecules may be used in a recombinant method for the production of PP13. Such methods are well known in the art and usually involve inserting the DNA molecule into an expression vector such as a plasmid, phage or viral DNA. The expression vector is then inserted into a compatible host cell such as bacterial cells, or eukaryotic cells such as yeast, plant, mammalian or insect cells. The host cell is incubated under conditions which induce expression of the inserted vector, thereby producing PP13.

For example, the DNA encoding PP13 can be inserted into an expression vector under the control of an inducible promotor such as the LacZ promoter, T7 or T4 polymerase promoter, heatshock promoters, etc. One example of an expression vector is the pQE expression vector (QIAGEN). The pQE vector provides high level expression of proteins containing a 6*His affinity tag in *E. coli*. The pQE contains a regulatable promoter consisting of the *E. coli* phage T5 promoter and two lac operator sequences. The vector is then inserted into a competent M15 [PREP4] *E. coli* strain (Villarejo and Zabin, 1974). The M15 host cell contains multiple copies of the plasmid pREPA which carries the lacI gene encoding the lac repressor. The host cell is incubated with IPTG which rapidly induces expression of the inserted vector, thereby producing PP13. Many other systems may also be used for PP13 expression, as is well known to the skilled artisan.

A kit for diagnosing pregnancy-related complications may be produced based on the present invention. Such a kit, for example, may comprise the following components: (1) antibodies capable of specifically binding PP-13; (2) labeled PP-13, for example by a radioactive, fluorescent or enzyme marker; (3) PP-13 standard solutions at known concentrations; and (4) means for detecting the signal produced in the assay. Such means could be, for example, antiserum raised against the PP-13-binding antibodies.

DETAILED DESCRIPTION OF THE DRAWINGS

The present invention will be better understood from the following detailed description of preferred embodiments, taken in conjunction with the following drawings in which:

FIG. 1 shows a partial nucleotide (SEQ ID NO:16) and deduced amino acid sequence (SEQ ID NO:17) of a cDNA from the Expressed Sequence Tag (EST) database (accession R24614). Regions that are similar to the sequenced peptides are underlined. PP13 derived peptide #3 (FIG. 1) was found to share partial identity with this cDNA (red underlined letters), and peptides #4, #5 and #6 are 100% identical to the EST database sequence. The nucleotide sequence of the 390-bp cDNA is shown with a translation of the open reading frame (118 amino acids). A Kozak-like translation initiation sequence containing a presumptive start codon (ATG) at nucleotide 33 is labeled with an asterisk. Nucleotide numbers are shown on the left.

FIG. 2 shows the complete nucleotide (SEQ ID NO:8) and deduced amino acid sequence (SEQ ID NO:9) of the PP13 cDNA clone as obtained from RACE analysis. The nucleotide sequence of the 611-bp cDNA is shown with translation of the open reading frame (139 amino acids). Regions that are identical to the digested peptide are numbered and underlined. A Kozak-like initiation of translation sequence containing a presumptive start codon (ATG) at nucleotide 41 is signed with asterisk. Nucleotide numbers are shown on the left.

FIG. 3 shows the alignment of amino acid sequence (SEQ ID NO:9) of PP13 and eosinophil lysophospholipase (SEQ. ID. NO:11). Identical amino acids of PP13 protein and eosinophil lysophospholipase (EPL) are designated by bold. There is about 54% identity between the two proteins.

DETAILED DESCRIPTION OF A PREFERRED EMBODIMENT

Materials and Methods

Materials

Modified trypsin and LysC (sequencing grade) were from Promega. Trifluoroacetic Acid (TFA) and hydrogenated TRITON X100 (RTX) were from Sigma. Ammonium Carbonate (AC) was from Riedel-de Haen. Acetonitrile (ACN) was from BioLab. 5' and 3' RACE Systems were from Gibco BRL. pUC57 cloning vector (T-Cloning Kit) was from MBI Fermentas.

Sequencing the PP13 Protein

The PP13 protein was immuno-affinity purified using rabbit polyclonal antibodies raised against placental proteins and affinity purified on the PP-13 protein. In order to further purify the PP-13 protein and to digest it with proteolytic enzymes, we used the method of Rosenfeld et al. (1992) as follows. The PP-13 protein was separated from other contaminating proteins by resolving it on SDS-PAGE in a mini gel format (10×10 cm) followed by fixing the gel and staining the gel with Coomassie brilliant blue. The gel was destained in 40% ethanol+10% acetic acid. The stained gel band containing the PP-13 protein was cut out with a clean razor blade and washed with 50% acetonitrile (ACN)+200 mM Ammonium Carbonate (AC) in water. This treatment was performed in order to remove as much as possible of the SDS, Coomassie brilliant blue and acetic acid. The washed gel piece was air dried for 30 minutes and rehydrated by adding to it 50–100 µl of 200 mM AC+1% RTX buffer containing 0.5 µgr modified trypsin or 0.5 µgr of LysC. After incubation with gentle shaking at 37° C. for 12 hours the proteolytic peptides released from the PP-13 protein were eluted from the gel piece by shaking it twice in 100 µl of 0.1% TFA+60% ACN at room temperature for 60 min. The solution was separated from the gel piece by centrifugation and dried down in a Speed-Vac to remove excess ACN. The proteolytic peptides were resolved by Reverse-phase HPLC on a Vydac 1×150 mm, C18, 300 column with a linear gradient from 4% ACN+0.1% TFA to 60% ACN+0.085% TFA at room temperature with a flow rate of 40 µl/min. The elution pattern of the peptides was determined by UV absorbance at 214 nm and fractions containing peptides were collected by hand into microfuge tube and stored at −80° C. Some of the fractions containing peptides were sequenced on a Protein-Peptide Sequencer (models 476A and 494A, Perkin Elmer) using the manufacturer's standard Edman chemistry and cycles.

cDNA 3' and 5' Ends Analysis

In order to isolate the full cDNA sequence of the PP-13 gene, we used a standard method called Rapid Amplification of cDNA Ends (RACE) (2) to extend both the 5' and 3' ends of the known parts of the cDNA to its ends. Generally, the RACE method generates cDNA by using a Polymerase Chain Reaction (PCR) to amplify copies of the region between known segments of the cDNA at specific points in the transcript and its 3' or 5' ends. This was accomplished by making copies of the cDNA between synthetic DNA primers complementary to known segments of the message to primers that anneal to the ends of the cDNA.

For the 3' prime end determination, reverse transcriptase (RT) reaction was carried out using 4 μgr of total placental RNA (prepared by TRI reagent from Molecular Research Center, Inc.) and the 3' end primer: (106ras) 5'-ggc cac gcg tcg act agt act ttt ttt ttt ttt tt-3' (SEQ ID NO:12). This was followed by a PCR reaction between the primers: (107 ras for the forward reaction) 5'-ggc cac gcg tcg act agt ac-3' (SEQ ID NO:13) and the reverse primer (100rs, homologous to peptide #4) was 5'-ggg ata tgg atg ttg gag gag ac-3' (SEQ ID NO:14). The PCR reaction included 2.5 mM MgCl$_2$, denaturation at 94° C. for 45", primer annealing at 60° C. for 45" and primer extension at 72° C. for 2 min. for 35 cycles.

For the 5' end determination the RT reaction was carried out with 4 μgr of total placental RNA and a specific 3' primer (101 ras): 5'-gtc tcc tcc aac atc cat atc-3' (SEQ ID NO:15). The 5' end of the cDNA was extended by adding to it poly-de using the RACE protocol and reagents (Gibco BRL). This was followed by a PCR reaction using conditions as above and the following primers: a backward primer with the abridged anchor primer (AAP) supplied by Gibco BRL and the forward reaction primer 101 rs described above.

The resulting PCR fragments were inserted into the pUC57-T cloning vector (T-Cloning Kit #K1212 MBI Fermentas) and clones containing the insert were selected and sequenced by automated DNA at the Biological Services at the Weizmann Institute, Rehovot, Israel.

Results

Identification of Peptides from PP13 Protein

In order to either clone the gene encoding the PP-13 protein or to identify its gene in one of the data banks, it was necessary to obtain the primary amino acid sequence of the PP-13 protein. Since the PP13 protein was blocked at its amino terminus, internal amino acid sequences were obtained after proteolytically digesting the protein into peptide fragments. These peptides were separated and purified by chromatography using reverse-phase HPLC, and some of the resolved peptides were sequenced. The amino acid sequences of the peptides that were successfully sequenced are listed in Table 1.

Table 1. Amino acid sequences of PP13 derived peptide fragments obtained after trypsin and LysC digestion as described above.

| Peptide number | Amino acid sequence |
| --- | --- |
| 1. (SEQ. ID. NO: 1) | LPVSLSVG |
| 2. (SEQ. ID. NO: 2) | VIIK |
| 3. (SEQ. ID. NO: 3) | GTPIHSFINDPQLQVDF |
| 4. (SEQ. ID. NO: 4) | EFGIWMLEETTDYVPFE |
| 5. (SEQ. ID. NO: 5) | QFELCIY |

-continued

| Peptide number | Amino acid sequence |
| --- | --- |
| 6. (SEQ. ID. NO: 6) | VHYNEY |
| 7. (SEQ. ID. NO: 7) | GFVHR |

Comparing Peptides Sequence to Data-Banks

DNA and protein data banks available through the Internet were searched for homology to the obtained PP-13 peptides sequences. A cDNA sequence (SEQ.ID.NO: 8) encoding four of the peptides fragments (FIG. 2) was identified (EST accession R24614). The fact that homology to more than one peptide sequence was present in the identified cDNA indicates that this cDNA is likely a product of the gene encoding the protein which is the major constituent of the PP13 preparation.

The sequence was found in an EST data bank created by the University of Washington and searched through the National Center for Biotechnology Information (NCBI) using the BLAST search program. The R24614 cDNA contains a Kozak-like translation initiation sequence and a 358 base-pair open reading frame (ORF) encoding a 118 amino acid polypeptide. The calculated molecular weight of the polypeptide encoded by the R24614 open reading frame is 13.9 Kda Four of the sequenced peptides have homology to parts of the deduced sequence of the large. open reading frame of the R24614 cDNA (FIG. 1). The obtained amino acid sequence of peptide #3 was found to share partial identity with the EST cDNA and peptides number 4, 5 and 6 were identical to different segments of the ORF in the R24614 sequence.

Since the open reading frame sequence of R24614 obtained from the data bank did not contain the entire coding region of the PP13 protein, it was necessary to obtain the full cDNA sequence.

Identification of PP13 Complete cDNA Sequence

In order to obtain full cDNA sequence we used Rapid Amplification of cDNA ends (RACE). Using the RACE method with an internal specific primers homologous to the sequence from the region of peptide 4 previously found (FIG. 1), we discovered the 3' and 5' end of PP13 message. The full PP13 amino acid sequence (SEQ.ID.NO: 9) and cDNA (SEQ.ID.NO: 10) are shown in FIG. 2.

The full cDNA contains a Kozak-like translation initiation sequence and a 417-bp open reading frame encoding a 139 amino acid polypeptide, with a predicted mass of 15.1 KDa which is about the same size of the molecular weight of the PP13 protein as calculated from its migration in SDS-PAGE. The major open reading frame of the full cDNA sequence contains all of the peptides sequence previously found by Edman sequencing of reverse-phase purified proteolytic peptides (FIG. 1).

Resemblance to Other Proteins

It turned out that the novel gene contains sequence similarity to eosinophil lysophospholipase (3), a protein of known significance in immunity and pregnancy disorders (FIG. 3). PP13 and eosinophil lysophospholipase have about 54% amino acid identity and 56% nucleic acid identity. The identity of the two proteins in the regions of the peptides, especially peptides number 4 and 6 is low, so it is clear that these proteins are different, but the homology and identity might suggests they belong to the same protein family.

REFERENCES

1. Rosenfeld et al. (1992) In-Gel digestion of protein for internal sequence analysis after one or two dimensional Gel Electrophoresis. Analytical Biochemistry, 203, 173–175.
2. Frohman, M. A., (1990) PCR Protocols: A Guide to Methods and Applications (Innis, M. A., Gelfand, D. H., Sninsky, J. J., and White, T. J, eds.) p. 28, Academic Press, San Diego.
3. Ackerman, S. J., Corrette, S. E., Rosenberg, H. F., Bennett, J. C., Mastrianni, D. M., Nicholson-Weller, A., Weller, P. F., Chin, D. T., and Tener, D. G. (1993) The J. of Immunology, 150, No. 2, pp 456–468.
4. Villarego, M. R. and Zabin, I. (1974) J. Bacteriol., 120, 466–474.

---

The invention claimed is:

1. An isolated Placental Protein 13 (PP13) protein consisting of SEQ ID NO:9.

2. An isolated Placental Protein 13 (PP13) protein comprising SEQ ID NO:9.

3. An isolated recombinant Placental Protein 13 (PP13) protein consisting of SEQ ID NO:9.

4. An isolated recombinant Placental Protein 13 (PP13) protein comprising SEQ ID NO:9.

5. A method of screening for pregnancy-related complications, comprising:
   (a) providing a serum sample of a pregnant woman;
   (b) determining the level of the protein of claim 1 in the serum sample; and
   (c) comparing said determined level with pre-determined normal levels for women at the same gestational age, a deviation between the levels being indicative of a pregnancy-related complication.

6. A method according to claim 5, wherein said pregnancy-related complication is selected from the group consisting of intrauterine growth retardation, preterm delivery and preeclampsia.

7. A kit for diagnosing pregnancy-related complications, comprising:
   (a) antibodies capable of specifically binding the protein of claim 1; and
   (b) PP13 prepared by a recombinant method for producing recombinant PP13, comprising:
      inserting a DNA molecule encoding the protein of claim 1 into an expression vector;
      inserting said expression vector into a host cell; and
      incubating said host cell under conditions which permit expression of the inserted vector, thereby producing recombinant PP13 consisting of SEQ ID NO:9.

8. A method of screening for pregnancy-related complications, comprising:
   (a) providing a serum sample of a pregnant woman;
   (b) determining the level of the protein of claim 3 in the serum sample; and
   (c) comparing said determined level with pre-determined normal levels for women at the same gestational age, a deviation between the levels being indicative of a pregnancy-related complication.

9. The method of claim 8, wherein said pregnancy-related complication is selected from the group consisting of intrauterine growth retardation, preterm delivery and preeclampsia.

* * * * *